(12) United States Patent
Kim

(10) Patent No.: US 6,180,619 B1
(45) Date of Patent: *Jan. 30, 2001

(54) PRENYL TRANSFERASE INHIBITORS

(75) Inventor: Sun H. Kim, Needham, MA (US)

(73) Assignee: Biomeasure, Incorporated, Milford, MA (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/098,393

(22) Filed: Jun. 16, 1998

Related U.S. Application Data

(63) Continuation-in-part of application No. 08/675,439, filed on Jun. 28, 1996.
(51) Int. Cl.$^7$ .......................... A61K 31/33; C07D 519/00
(52) U.S. Cl. .......................... 514/183; 540/453; 540/455; 544/359; 544/361; 544/363; 544/399; 514/250; 514/255
(58) Field of Search .................................. 514/255, 252, 514/250, 183; 544/391, 359, 361, 363, 387, 399; 540/453, 455

(56) References Cited

U.S. PATENT DOCUMENTS 5,736,539 * 4/1998 Graham et al. ...................... 514/218

* cited by examiner

Primary Examiner—Alan L. Rotman
Assistant Examiner—Charanjit S. Aulakh
(74) Attorney, Agent, or Firm—John D. Conway; Brian R. Morrill; Fish & Richardson

(57) ABSTRACT

A family of compounds capable of inhibiting the activity of prenyl transferases. The compounds are covered by the four following formulas

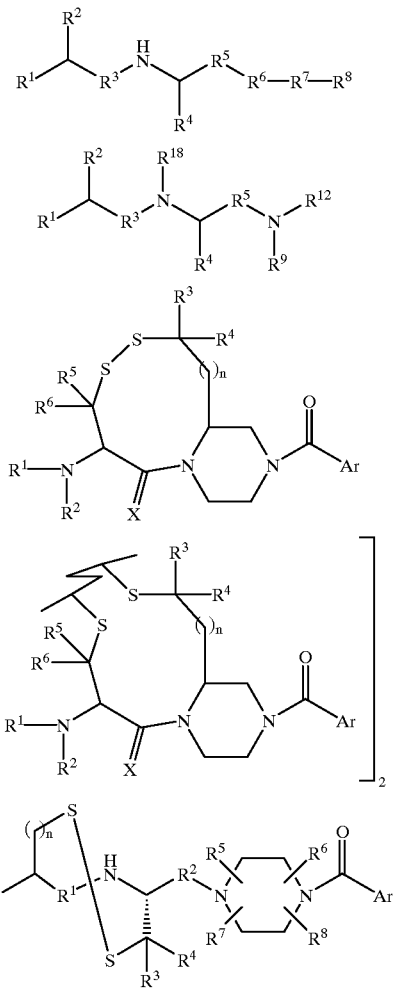

Each of the R groups is defined in the disclosure.

7 Claims, No Drawings

PRENYL TRANSFERASE INHIBITORS

CROSS-REFERENCE TO RELATED APPLICATION

This application is a continuation-in-part of U.S. patent application Ser. No. 08/675,439, filed Jun. 28, 1996.

BACKGROUND OF THE INVENTION

The Ras family of proteins are important in the signal transduction pathway modulating cell growth. The protein is produced in the ribosome, released into the cytosol, and post-translationally modified. The first step in the series of post-translational modifications is the alkylation of $Cys^{168}$ with farnesyl or geranylgeranyl pyrophosphate in a reaction catalyzed by prenyl transferase enzymes such as farnesyl transferase and geranylgeranyl transferase (Hancock, J F, et al., Cell 57:1167–1177 (1989)). Subsequently, the three C-terminal amino acids are cleaved (Gutierrez, L., et al., EMBO J. 8:1093–1098 (1989)), and the terminal Cys is converted to a methyl ester (Clark, S., et al., Proc. Nat'l Acad. Sci. (USA) 85:4643–4647 (1988)). Some forms of Ras are also reversibly palmitoylated on cysteine residues immediately N-terminal to $Cys^{168}$ (Buss, J E, et al., Mol. Cell. Biol. 6:116–122 (1986)). It is believed that these modifications increase the hydrophobicity of the C-terminal region of Ras, causing it to localize at the surface of the cell membrane. Localization of Ras to the cell membrane is necessary for signal transduction (Willumsen, B M, et al., Science 310:583–586 (1984)).

Oncogenic forms of Ras are observed in a relatively large number of cancers including over 50 percent of colon cancers and over 90 percent of pancreatic cancers (Bos, J L, Cancer Research 49:4682–4689 (1989)). These observations suggest that intervention in the function of Ras mediated signal transduction may be useful in the treatment of cancer.

Previously, it has been shown that the C-terminal tetrapeptide of Ras has the "CAAX" motif (wherein C is cysteine, A is an aliphatic amino acid, and X is any amino acid). Tetrapeptides having this structure have been shown to be inhibitors of prenyl transferases (Reiss, et al., Cell 62:81–88 (1990)). Poor potency of these early farnesyl transferase inhibitors has prompted the search for new inhibitors with more favorable pharmacokinetic behavior (James, G L, et al., Science 260:1937–1942 (1993); Kohl, N E, et al., Proc. Nat'l Acad. Sci. USA 91:9141–9145 (1994); deSolms, S J, et al., J. Med. Chem. 38:3967–3971 (1995); Nagasu, T, et al., Cancer Research 55:5310–5314 (1995); Lerner, E C, et al., J. Biol. Chem. 270:26802–26806 (1995); Lerner, E C, et al., J. Biol. Chem. 270:26770 (1995); and James, et al., Proc. Natl. Acad. Sci. USA 93:4454 (1996)).

Recently, it has been shown that a prenyl transferase inhibitor can block growth of Ras-dependent tumors in nude mice (Kohl, N E, et al., Proc. Nat'l Acad. Sci. USA 91:9141–9145 (1994)). In addition, it has been shown that over 70 percent of a large sampling of tumor cell lines are inhibited by prenyl transferase inhibitors with selectivity over non-transformed epithelial cells (Sepp-Lorenzino, I, et al., Cancer Research, 55:5302–5309 (1995)). Inhibiting farnesylation has been disclosed as a method of treating hepatitis delta virus infection, (Casey, P, et al., WO 97/31641).

SUMMARY OF THE INVENTION

In one aspect, the invention features a compound of formula I or formula II

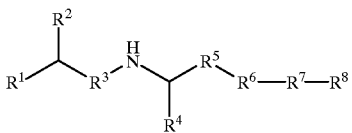

Formula I

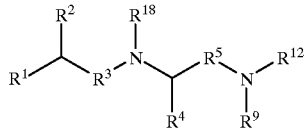

Formula II wherein
$R^1$ is $N(R^{10})(R^{11})$;
$R^2$ is thio lower alkyl;
each of $R^3$ and $R^5$, independently, is $CH_2$ or $C(O)$;
$R^4$ is substituted or unsubstituted thio lower alkyl, wherein said substituent is $CH_2NHC(O)R^{13}$ and said substituent is attached to said thio group;
$R^6$ is a residue of a natural or synthetic α-amino acid;
$R^7$ is a residue of a natural or synthetic α-amino acid;
$R^8$ is OH or lower alkoxy, or, together with $R^7$, forms homoserinelactone;
each of $R^9$, $R^{10}$ and $R^{11}$, independently, is H or lower alkyl;
$R^{12}$ is substituted or unsubstituted cycloalkyl, cycloalkyl lower alkyl, aryl, aryl lower alkyl, heterocycle, or heterocycle lower alkyl, wherein said substituent is lower alkyl, aryl, halo, lower alkoxy, or $C(O)-R^7-R^8$;
$R^{13}$ is lower alkyl, aryl, or aryl lower alkyl;
$R^{18}$ is H or, together with $R^9$, forms $CH_2CH_2$;
provided if $R^4$ is unsubstituted thio lower alkyl, the free thio group of $R^2$ and the free thio group of $R^4$ may form a disulfide bond;
or a pharmaceutically acceptable salt thereof.

In another aspect, the present invention is directed to a process for preparing a compound of Formula I or Formula II.

In one embodiment, the compound is of formula I where $R^6$ is $-N(R^{14})CH(R^{15})C(O)-$, where $R^{14}$ is H or lower alkyl, and $R^{15}$ is substituted or unsubstituted lower alkyl, aryl, aryl lower alkyl, heterocycle, or heterocycle lower alkyl where said substituent is lower alkyl, halo, or lower alkoxy, or where $R^{15}$, together with $NR^{14}C$ attached thereto, form heterocycle; and $R^7$ is $-N(R^{16})CH(R^{17})C(O)-$ where $R^{16}$ is H or lower alkyl, and $R^{17}$ is $(CH_2)_mS(O)_nCH_3$ or substituted or unsubstituted lower alkyl, thio lower alkyl, where said substituent is $C(O)N(R^{10})(R^{11})$, m is 1–6, n is 0–2, and $R^8$ is OH or lower alkoxy. In this embodiment, $R^2$ can be $CH_2SH$; $R^4$ can be $C(CH_3)_2SH$ or $CH_2SH$ wherein the free thio group of $R^2$ and the free thio group of $R^4$ form a disulfide bond; $R^{15}$, together with $NR^{14}C$ attached thereto, can form heterocycle; $R^{16}$ can be H; and $R^{17}$ can be $(CH_2)_2S(O)_nCH_3$; furthermore, $R^1$ can be $NH_2$; $R^3$ can be $CH_2$; $R^5$ can be CO; and $R^8$ can be OH or $OCH_3$. In the same embodiment, $R^2$ can be $(CH_2)SH$; $R^4$ can be $C(CH_2)_2SCH_2NHCOCH_3$ or $CH_2SCH_2NHCOCH_3$; $R^{15}$, together with $NR^{14}C$ attached thereto, can form heterocycle; $R^{16}$ can be H, and $R^{17}$ can be $(CH_2)_2S(O)_nCH_3$; furthermore, $R^1$ is $NH_2$; $R^3$ is $CH_2$; $R^5$ is C(O); and $R^8$ is OH or $OCH_3$.

In another embodiment, the compound is of formula II, wherein $R^2$ is $CH_2SH$; $R^4$ is $C(CH_3)_2SH$ or $CH_2SH$ wherein the free thio group of $R^2$ and the free thio group of $R^4$ form a disulfide bond; $R^{12}$ is substituted or unsubstituted aryl or aryl lower alkyl, and $R^{18}$ is H. In this embodiment, $R^1$ can be $NH_2$; $R^3$ can be $CH_2$; $R^5$ can be C(O); $R^9$ can be H; and $R^{12}$ can be substituted or unsubstituted phenyl or benzyl, wherein said substituent is lower alkyl or halo.

In a still further embodiment, $R^2$ is $(CH_2)SH$; $R^4$ is $C(CH_2)_2SCH_2NHCOCH_3$ or $CH_2SCH_2NHCOCH_3$; and $R^{12}$ is substituted or unsubstituted aryl or aryl lower alkyl. In this embodiment, $R^1$ can be $NH_2$; R can be $CH_2$; $R^5$ can be CO; $R^9$ can be H; and $R^{12}$ can be substituted or unsubstituted phenyl or benzyl, wherein said substituent is lower alkyl or halo.

Examples of the present invention include the following:

compound 1
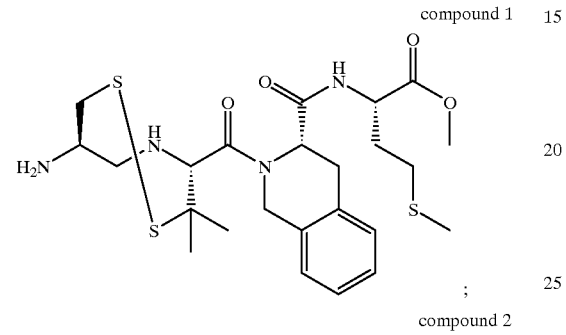
;

compound 2
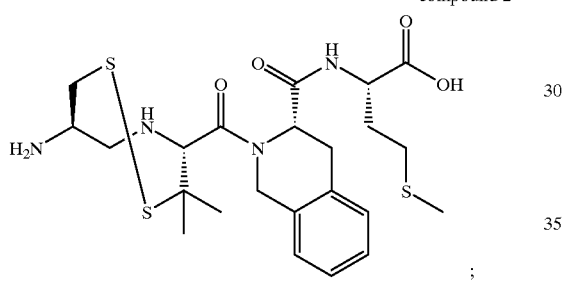
;

compound 3
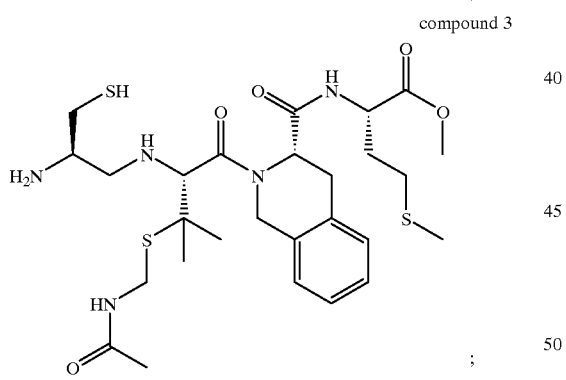
;

compound 4
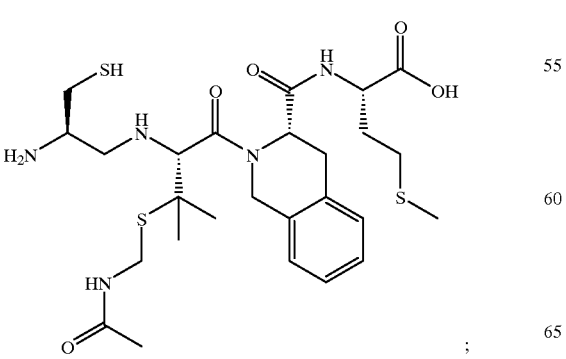
;

compound 5
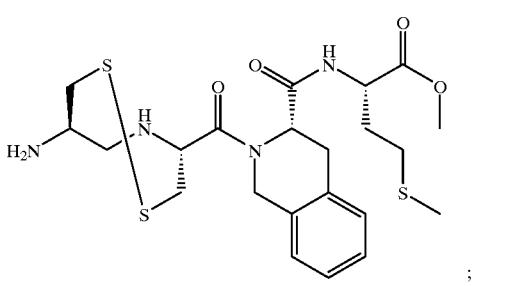
;

compound 6
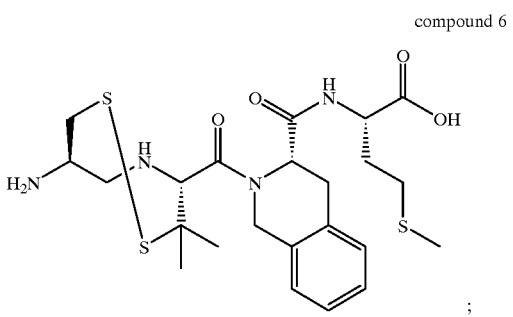
;

compound 7
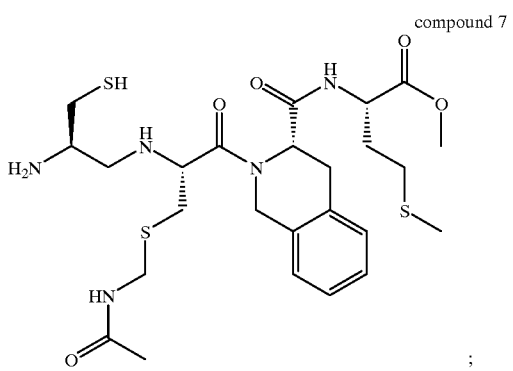
;

compound 8
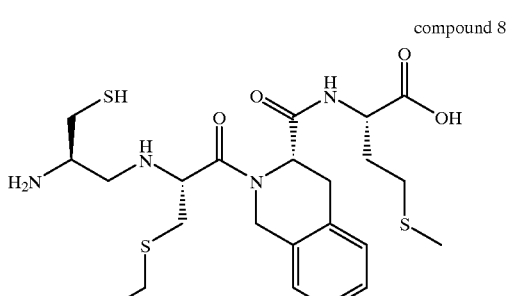
;

compound 9
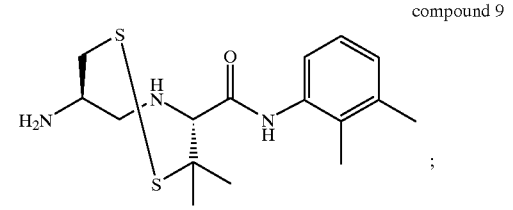
;

compound 10
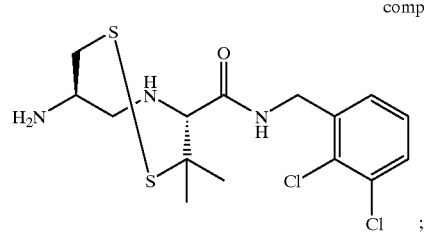
;
compound 11
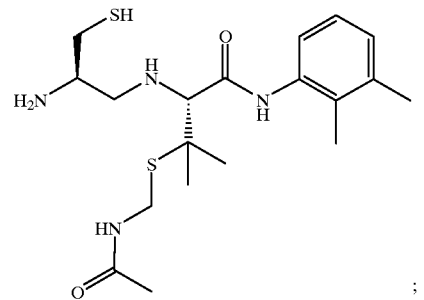
;
compound 12
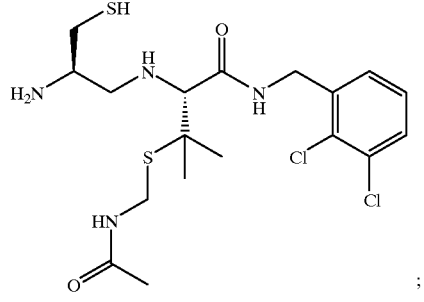
;
compound 13
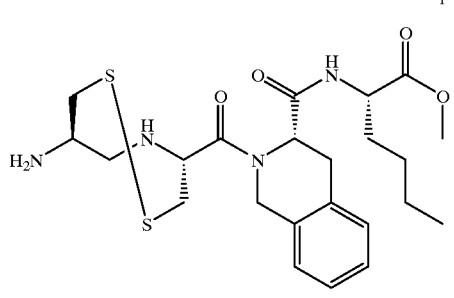
;
compound 14
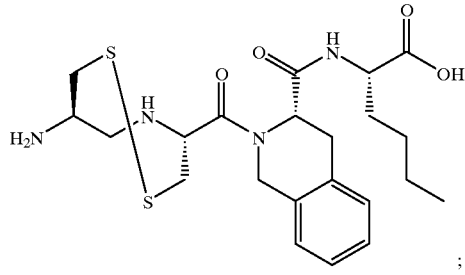
;
compound 15
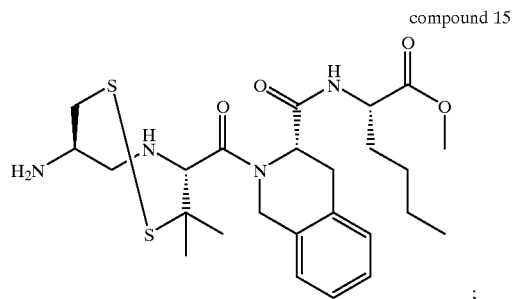
;
compound 16
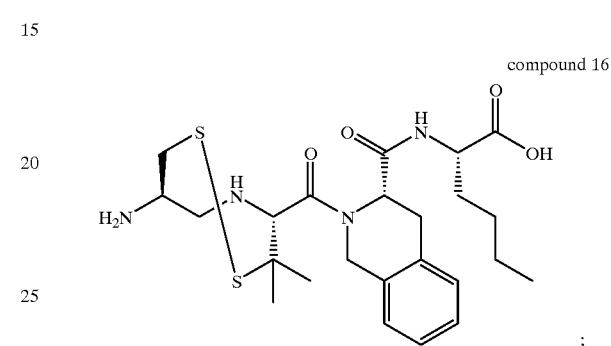
;
compound 17
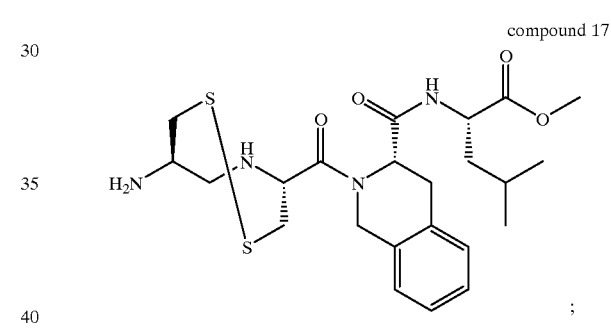
;
compound 18
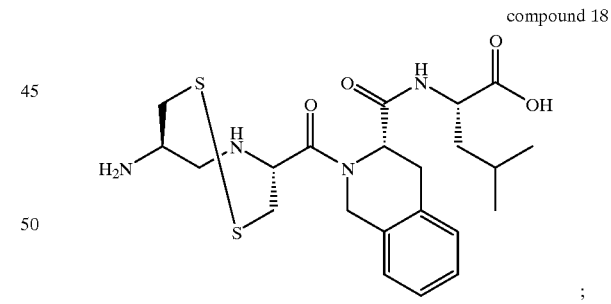
;
compound 19
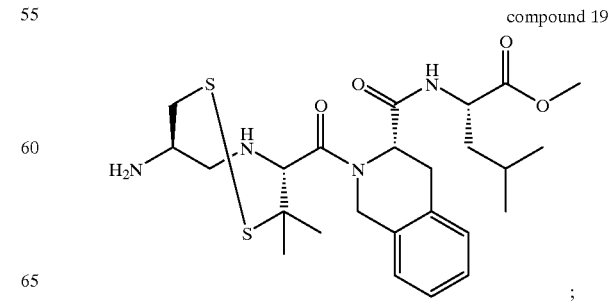
;

-continued compound 20
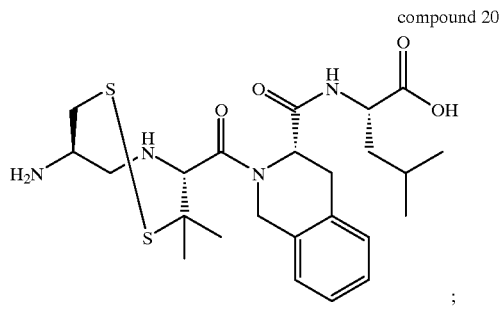
;

compound 23
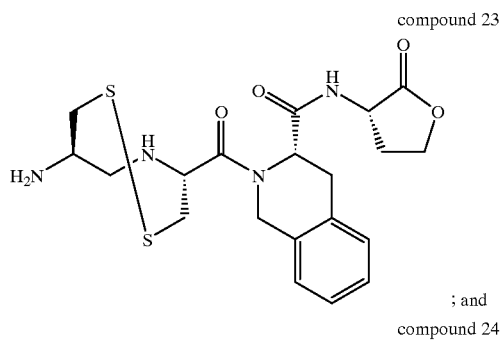
; and compound 24
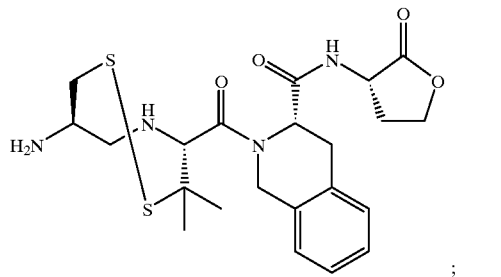
;

In another aspect, the invention features a compound of formula III or formula IV Formula III
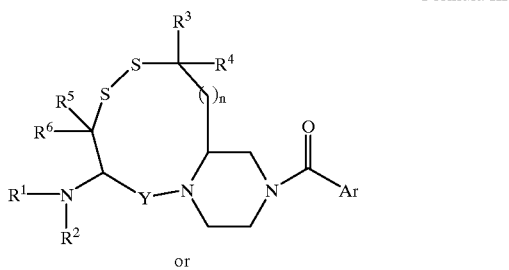
or Formula IV
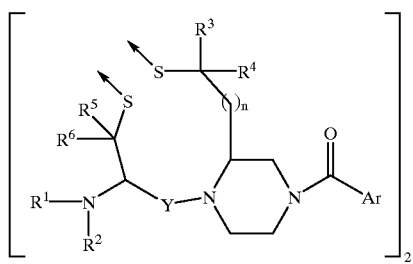

where

Y is $CH_2$ or $C(O)$;

$R^1$, $R^2$, $R^3$, and $R^4$, each is, independently, H, lower alkyl, optionally substituted arylalkyl, optionally substituted alkenyl, $(C_1-C_{18})$-aliphatic acyl, or arylacyl;

$R^5$ and $R^6$ each is, independently, H or $CH_3$;

$R_9$ and $R_{10}$ each is independently selected from the group consisting of H, lower alkyl, and $C_3-C_6$ cycloalkyl;

Ar is optionally substituted aryl or optionally substituted heterocycle;

n is 0 or an integer from 1 to 4;

wherein each substituent is, independently, aryl, heterocycle, halogen, $OR^9$, $NR^9R^{10}$, CN, $NO_2$, $CF_3$, or lower alkyl, said lower alkyl optionally substituted with $C_1-C_4$ alkoxy, $NR^9R^{10}$, $C_3-C_6$ cycloalkyl, or OH;

or a pharmaceutically acceptable salt thereof.

In still another aspect, the present invention is directed to a process for preparing a compound of Formula III or Formula IV.

A preferred group of compounds of Formula III or Formula IV include the following:

compound 21
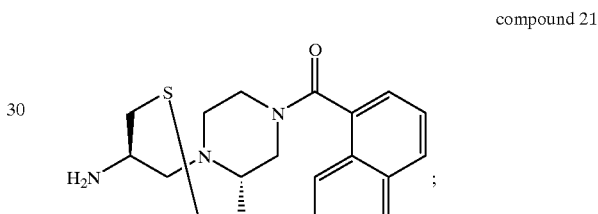
;

compound 22
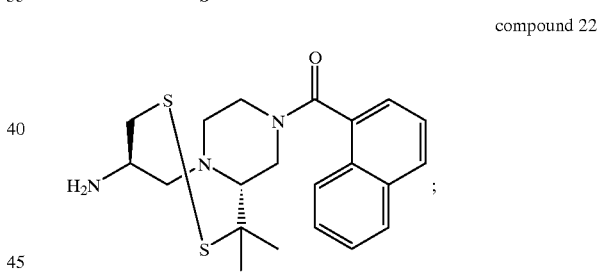
;

compound 28
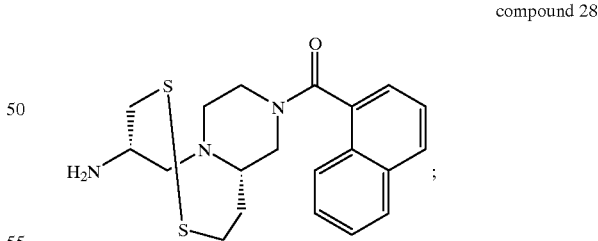
;

compound 29
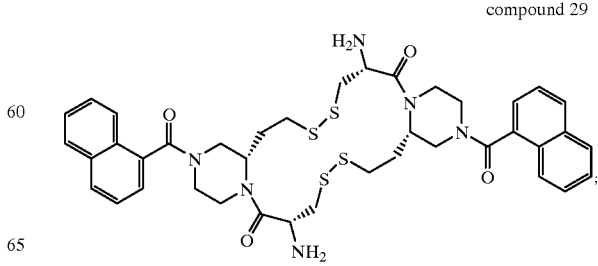
;

-continued

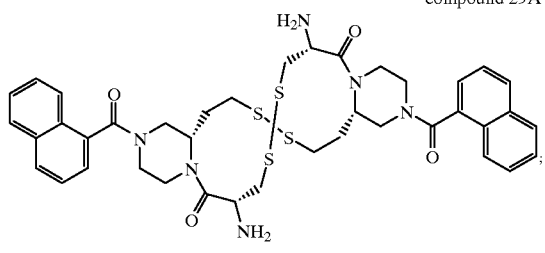
compound 29A and

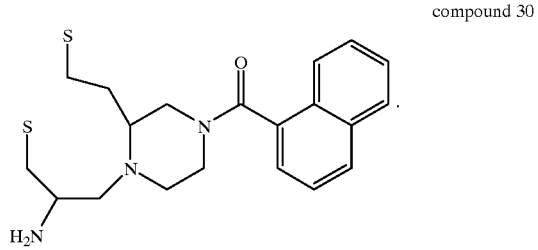
compound 30

In yet another aspect, the invention features a compound of formula V:

Formula V
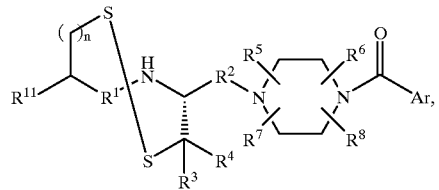

wherein
Ar is optionally substituted aryl or optionally substituted heterocycle, wherein each substituent is independently selected from the group consisting of aryl, heterocycle, halogen, $OR^9$, $N^9R^{10}$, CN, $NO_2$, $CF_3$, and lower alkyl, said lower alkyl optionally substituted with ($C_1$–$C_4$)-alkoxy, $NR^9R^{10}$, $C_3$–$C_6$ cycloalkyl, or OH;
$R^1$ and $R^2$ each is, independently, $CH_2$ or C(O);
$R^3$ and $R^4$ each is, independently, H or $CH_3$;
$R^5$, $R^6$, $R^7$, and $R^8$ each is independently selected from the group consisting of H, or an optionally substituted moiety selected from the group consisting of ($C_1$–$C_8$)-alkyl, alkenyl, alkynyl, aryl, and heterocycle;
wherein said optionally substituted moiety is optionally substituted by one or more substituents independently selected from the group consisting of ($C_3$–$C_6$)-cycloalkyl, optionally further substituted aryl, and optionally further substituted heterocycle, wherein said optionally further substituted aryl and heterocycle are optionally substituted by one or more substituents independently selected from the group consisting of ($C_1$–$C_4$)-alkyl, halogen, $(CH_2)_m$ $OR^9$, and $(CH_2)_m NR^9R^{10}$;
$R^9$ and $R^{10}$ each is, independently, H lower alkyl or ($C_3$–$C_6$) cycloalkyl;
$R^{11}$ is H or $NH_2$;
m is 0 or an integer from 1 to 4;
n is 0, 1, or 2;
or a pharmaceutically acceptable salt thereof.

In another aspect, the present invention is directed to a process for preparing a compound of Formula V.
A preferred group of compounds of Formula V includes the following:

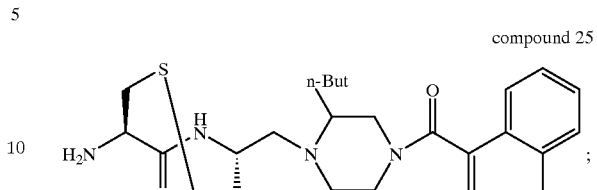
compound 25

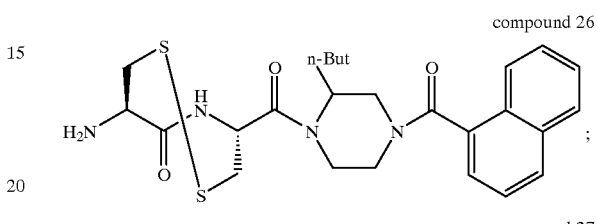
compound 26

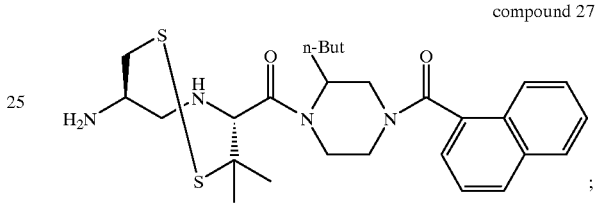
compound 27 and

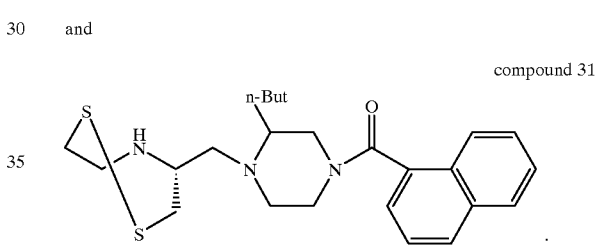
compound 31

The compounds of the present invention may have asymmetric centers and occur as racemates, racemic mixtures, and as individual diastereomers, with all possible isomers, including optical isomers, being included in the present invention. For simplicity, where no specific configuration is depicted in a structural formula, it is understood that all enantiomeric forms and mixtures thereof are represented.

As used herein, "lower alkyl" is intended to include saturated aliphatic hydrocarbon groups having 1–6 carbon atoms. Examples of lower alkyl groups include methyl, ethyl, propyl, isopropyl, butyl, isobutyl, sec-butyl, t-butyl, and the like. The term "alkyl" refers to saturated aliphatic hydrocarbon groups having up to 18 carbon atoms. The terms "alkenyl" and "alkynyl" refer to unsaturated aliphatic hydrocarbon groups having 2–18 carbon atoms and from 1 to 5 double or triple bonds. "Lower alkoxy" groups include those groups having 1–6 carbons. Examples of lower alkoxy groups include methoxy, ethoxy, propoxy, isopropoxy, and the like. All alkyl, alkenyl, alkynyl and alkoxy groups may be branched or straight chained, but are noncyclic. The term "cycloalkyl" means a 3–7 carbon ring. Examples of cycloalkyl groups include cyclopropyl, cyclobutyl, cyclopentyl, cyclohexyl, and cycloseptyl. The term "halo" means chloro, bromo, iodo, or fluoro. The terms "heterocycle lower alkyl," "thio lower alkyl," "cycloalkyl lower alkyl", and "lower alkyl," are substituted, respectively, with one to three heterocycle, thio, cycloalkyl, and aryl groups.

As used herein, "aryl" is intended to include any stable monocyclic, bicyclic, or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl, and the like.

The term heterocycle, as used herein, represents a stable 5- to 7-membered monocyclic or stable 8- to 11-membered bicyclic or stable 11 to 15-membered tricyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thiazolidinyl, thienofuryl, thienothienyl, thienyl, and the like.

When a group is substituted, it may be substituted one to four times. The various substituents may be attached to carbon atoms or to heteroatoms (e.g., S, N, or O).

As used herein, the term "residue of an α-amino acid" stands for an α-amino acid residue which is either a natural α-amino acid which is found in nature (e.g., cysteinyl, methionyl, phenylalaninyl, leucinyl, etc.) or a synthetic α-amino acid which is not found in nature (e.g., neurleucyl or the residue of 1,2,3,4-tetrahydroisoquinoline-3-carboxylic acid or penicillamine, etc.).

The compounds of this invention can be provided in the form of pharmaceutically acceptable salts. Acceptable salts include, but are not limited to acid addition salts of inorganic acids such as acetate, maleate, fumarate, tartrate, succinate, citrate, lactate, methanesulfonate, p-toluenesulfonate, pamoate, salicylate, oxalate, and stearate. Also within the scope of the present invention, where applicable, are salts formed from bases such as sodium or potassium hydroxide. For further examples of pharmaceutically acceptable salts see, "Pharmaceutical Salts," J. Pharm. Sci. 66:1 (1977).

In another aspect, the invention features a method of inhibiting prenyl transferases (e.g., farnesyl transferase or geranylgeranyl transferase) in a subject, e.g., a mammal such as a human, by administering to the subject a therapeutically effective amount of a compound of formula I, formula II, formula III, formula IV, or formula V. In particular, the present invention also covers a method of treating restenosis or tissue proliferative diseases (i.e., tumor) in a subject by administering to the subject a therapeutically effective amount of a compound or its salt. Examples of a tissue proliferative disease include both those associated with benign (e.g., non-malignant) cell proliferation such as fibrosis, benign prostatic hyperplasia, atherosclerosis, and restenosis, and those associated with malignant cell proliferation, such as cancer (e.g., ras-mutant tumors). Examples of treatable tumors include breast, colon, pancreas, prostate, lung, ovarian, epidermal, and hematopoietic cancers (Sepp-Lorenzino, I, et al., Cancer Research 55:5302 (1995)).

A therapeutically effective amount of a compound of this invention and a pharmaceutically acceptable carrier substance (e.g., magnesium carbonate, lactose, or a phospholipid with which the therapeutic compound can form a micelle) together form a pharmaceutical composition (e.g., a pill, tablet, capsule, or liquid) for administration (e.g., orally, intravenously, transdermally, or subcutaneously) to a subject in need of the compound. The pill, tablet, or capsule can be coated with a substance capable of protecting the composition from the gastric acid or intestinal enzymes in the subject's stomach for a period of time sufficient to allow the composition to pass undigested into the subject's small intestine.

The compounds of the present invention may be administered in a dosage range of about 0.0001 to 200 mg/kg/day, preferably 0.01 to 100 mg/kg/day. A dose of a compound of the present invention for treating the above-mentioned diseases or disorders varies depending upon the manner of administration, the age and the body weight of the subject, and the condition of the subject to be treated, and ultimately will be decided by the attending physician or veterinarian. Such an amount of the compound as determined by the attending physician or veterinarian is referred to herein as a "therapeutically effective amount."

Also contemplated within the scope of the invention are a method of preparing the compounds of formula I, formula II, formula III, formula IV, and formula V, and the novel chemical intermediates used in these syntheses as described herein.

Other features and advantages of the present invention will be apparent from the detailed description of the invention and from the claims.

DETAILED DESCRIPTION OF THE INVENTION

It is believed that one skilled in the art can, based on the description herein, utilize the present invention to its fullest extent. The following specific embodiments are, therefore, to be construed as merely illustrative, and not limitative of the remainder of the disclosure in any way whatsoever.

A compound of the present invention can be tested for farnesyl transferase inhibiting activity by testing said compound in a farnesyl transferase in vitro assay, such as the assay described below.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

Farnesyl transferase activity is assayed by [$^3$H] farnesylation of recombinant human H-Ras protein wild type, using microplate and filtration method. Incubation mixture contains, in a total volume of 25 $\mu$l: 50 mM Tris HCl (pH 7.5), 5 mM dithiothreitol, 20 $\mu$M $ZnCl_2$, 40 mM $MgCl_2$, 0.6 $\mu$M [$^3$H] farnesyl pyrophosphate (22.3 Ci/mmol), 4 $\mu$M H-Ras and 10 $\mu$g of farnesyl transferase from human brain cytosol. Test compounds are added in adequate solvent and incubations start by addition of farnesyl transferase. After approximately 60 minutes at approximately 37° C., the reaction is stopped by addition of 100 $\mu$l of 10% HCl in ethanol and allowed to incubate approximately 15 minutes at approximately 37° C., then 150 $\mu$l of absolute ethanol are added and incubation mixture is filtered on Unifilter GF/B microplates and washed 6 times with ethanol. After addition of 50 $\mu$l of Microscint 0, plates were counted on a Packard Top Count scintillation counter. Geranylgeranyl transferase activity is assayed by the same method, but using 4 $\mu$M human recombinant H-Ras CVLL type, 0.6 $\mu$M [$^3$H] geranylgeranyl-pyrophosphate (19.3 Ci/mmmol) and 100 $\mu$g of geranylgeranyl transferase from human brain.

The following is a description of the synthesis of compounds 1, 4, 9. Compounds 2,3,5–8, 10–20 can be prepared in an analogous manner by a person of ordinary skill in the art using appropriate starting materials. Compounds 21, 28, 29, and 30 were prepared using the reactions summarized in reaction scheme I. Compound 22 was prepared using the reactions summarized in reaction schemes II and IV. Compounds 25, 26, and 27 were prepared using the reactions summarized in reaction scheme V. Compound 31 may be prepared using the reactions summarized in scheme III. Other compounds of the invention can be prepared in an analogous manner by a person of ordinary skill in the art using appropriate starting materials.

The compounds of the invention were prepared using standard solution phase methodologies, e.g., as described in Greenstein, et al., Chemistry of the Amino Acids, Vols. 1–3 (J. Wiley, New York (1961)); and M. Bodanszky, et al., The Practice of Peptide Synthesis (Springer-Verlag, 1984)). The condensation reactions were carried out in an inert organic solvent, e.g., dimethylformide, dichloromethane, tetrahydrofuran, benzene or acetonitrile, using a suitable mild condensing agent, e.g., 1-(3-dimethylaminopropyl)-3-ethylcarbodiimide-HCl (EDC), 0-benzotriazol-1-yl-N,N,N', N'-tetramethyluronium hexafluorophosphate (HBTU), and optionally a catalyst, e.g., 1-hydroxybenzotriazole (HOBT). The reaction temperature was maintained below room temperature (−15° C. to room temperature) in order to minimize side reactions. Cyclic disulfide formation was carried out under high dilute condition using using various oxidizing agents (e.g. oxygen, iodine, immobilized oxidizing agent like EKATHIOX™ resin, (Ekagen Corp., Menlo Park, Calif., etc.)), in various solvents (e.g. water, alcohol, acetonitrile, tetrahydrofuran (THF), acetic acid, chloroform, etc.). See, e.g., B. Kamber, et al., Helv. Chim. Acta, 63(96):899 (1980). Compounds where $R^8$, together with $R^9$, forms $CH_2CH_2$ can be made according to the methods of Williams, et al., J. Med. Chem. 39(7):1346 (1996), e.g., by starting with protected cysteine.

2-Alkylpiperazines were synthesized similarly according to the procedure described in Org. Prep. Proc. Int. 1990, 22, 761–768. Replacement of hydroxyl group by protected sulfur were carried out by Mitsunobu reactions. (Synthesis 1981, 1; Tet. Lett. 1981, 3119 etc.) The protected cysteinal was prepared according to the procedure put forth by O. P. Goel, et al., (Org. Syn. 1988, 67, 69–75). The reductive alkylation can be accomplished with various agents, e.g. sodium triacetoxyborohydride, $(Na(OAc)_3BH)$, sodium cyanoborohydride or pyridine-borane complex, in solvents such as dichloromethane, dichloroethane, methanol or dimethylformamide, etc.

The intermediate and final products were isolated and purified by standard methods, e.g., column chromatography or HPLC.

REACTION SCHEME I

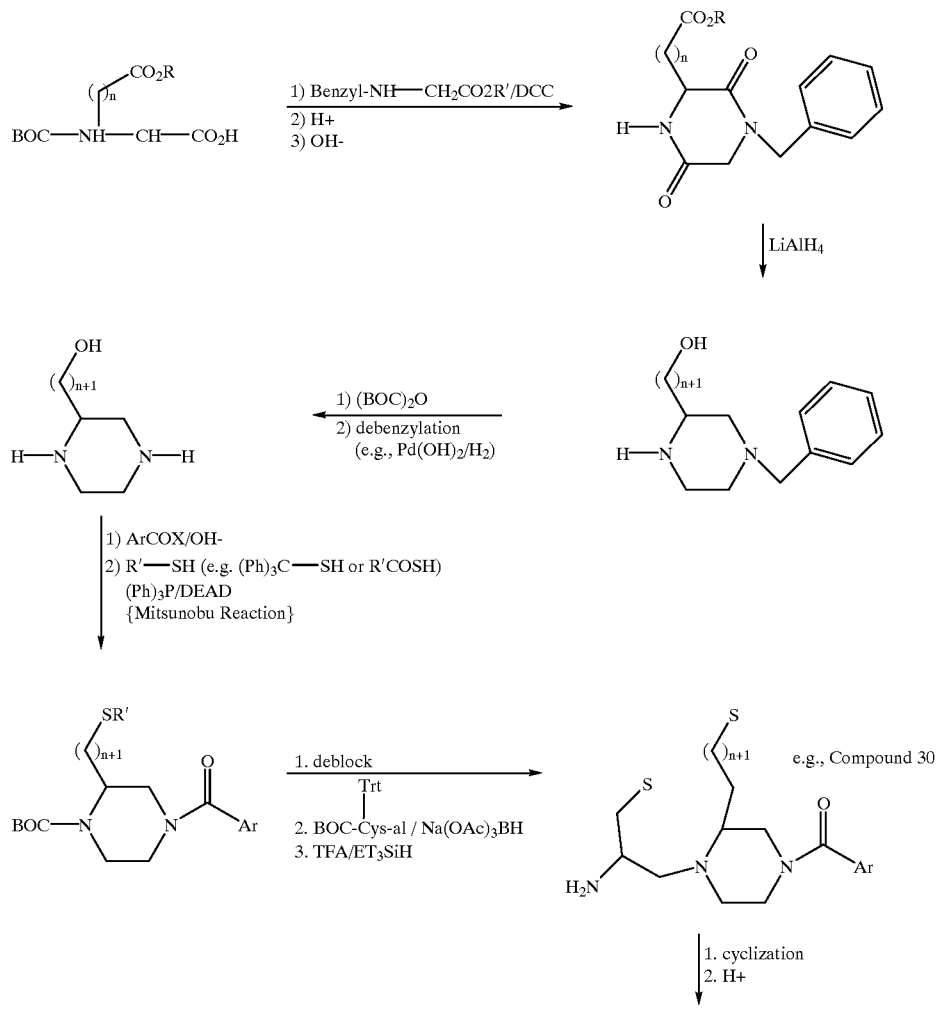

e.g., Compound 28
n = 0 or an integer from 1 to 4
Cys-al = Cysteinal
REACTION SCHEME II
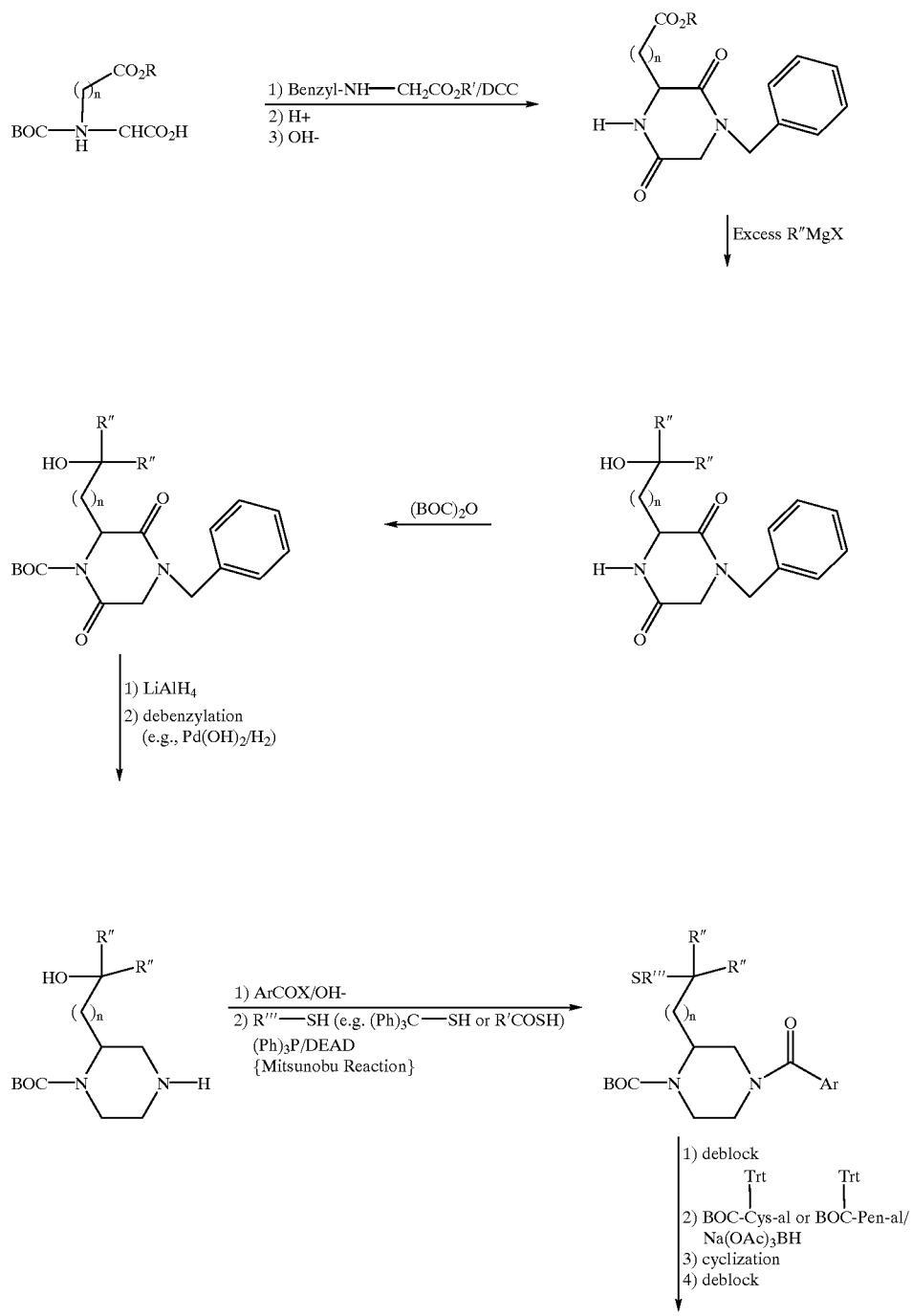

-continued
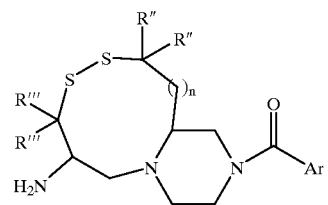
n = 0 or an integer from 1 to 4
R''' = H or CH₃;
Cys = Cysteine, Cys-al = Cysteinal;
Pen = Penicillamine, Pen-al = Pennicillaminylal
REACTION SCHEME III
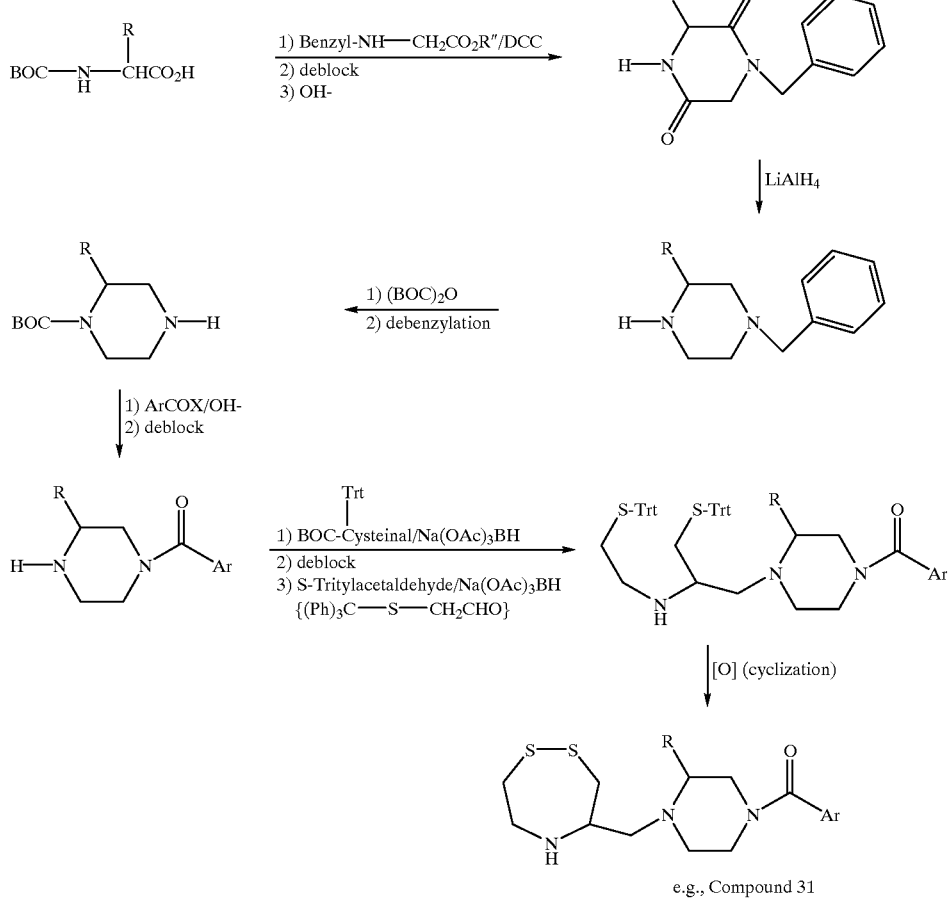
e.g., Compound 31
REACTION SCHEME IV
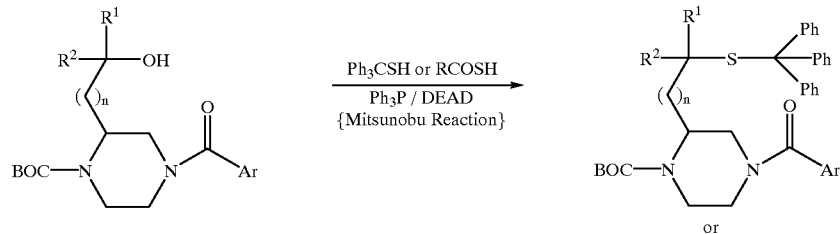
or

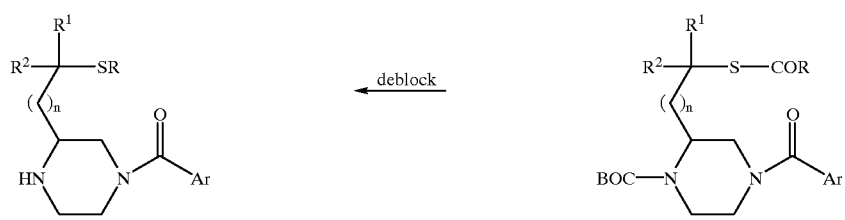
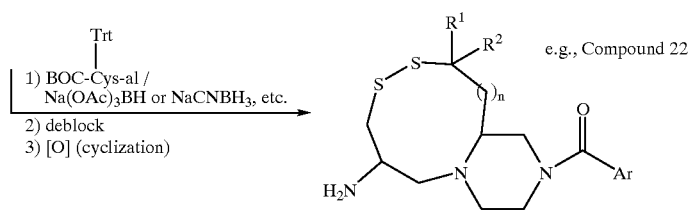
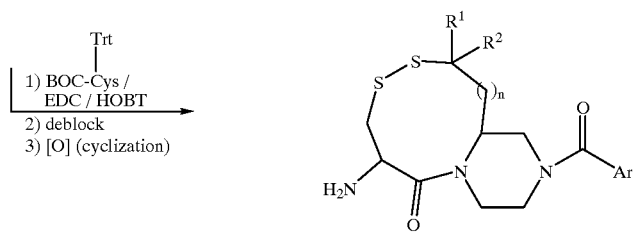
n = an integer from 1 to 4
Cys = Cysteine, Cys-al = Cysteinal
REACTION SCHEME V
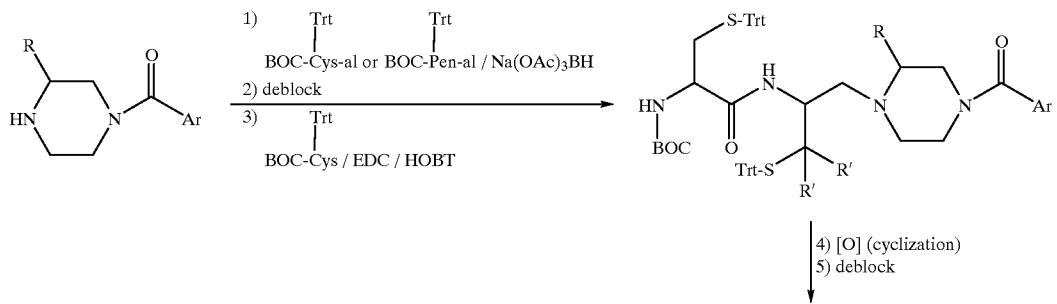
e.g., Compound 25
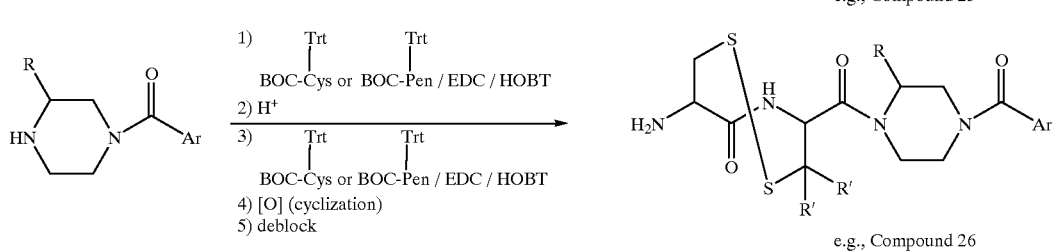
e.g., Compound 26

-continued

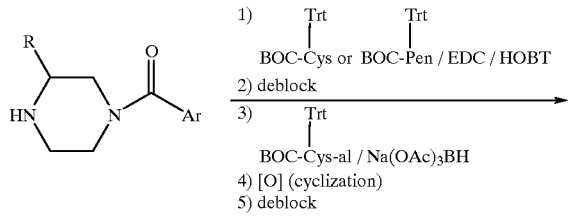 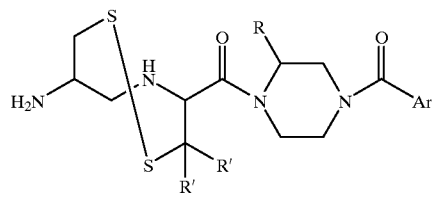

e.g., Compound 27

R' = H or CH₃;
Cys = Cysteine, Cys-al = Cysteinal;
Pen = Penicillamine, Pen-al = Penicillaminylal

Example 1

Synthesis of N-[2-(R)-amino-3-mercaptopropyl]-L-penicillaminyl-1,2,3,4-tetrahydro-3(s)-isoquinoline Carbonyl Methionine Methylester Cyclic Disulfide (Compound 1)

a) N-t-Butoxycarbonyl-S-trityl-L-cysteinyl-N,O-dimethylamide

To an ice-cooled solution of N-t-butoxycarbonyl-L-cysteine (8.0 g) and N,O-dimethylhydroxylamine hydrochloride (7.1 g) in 80 ml dimethylformide was added 4.2 ml diethylcyanophosphonate and 14.7 ml diisopropylethylamine, and after stirring at 0° C. for about 1 hour, the reaction mixture was allowed to room temperature overnight. Volatile substances were removed in vacuo to dryness, and the residue was partitioned between ethylacetate and water. Ethylacetate layer was washed with aqueous NaHCO₃, water, and dried (MgSO₄). Solvent was evaporated in vacuo to dryness, and the residue was chromatographed on silica gel (165 g) using CHCl₃ as an eluant. Appropriate fractions were pooled, and solvent was removed in vacuo to dryness. White foam 8.08 g TLC (silica gel: CHCl₃/acetone=9:1 R$_f$=0.58).

b) 2(R)-t-Butoxycarbonylamino-3-triphenylmethylmercaptopropanal

To an ice-cooled solution of N-t-Butoxycarbonyl s-trityl-L-cysteinyl-N,O-dimethylamide (0.85 g) in 20 ml tetrahydrofuran (THF) was added dropwise 3 ml 1.0 M LiAH₄ in THF under nitrogen atmosphere. After the mixture was stirred for about 30 minutes at 0° C., 1M KHSO₄ was slowly added, and the resulting emulsion was filtered through diatomaceous earth pad and further washed with ethylacetate. After drying over anhydrous MgSO₄, the solvent was removed in vacuo to dryness resulting in 0.7 g of the above-titled compound TLC (silica gel; CHCl₃/acetone=4:1; R$_f$=0.88).

c) N-t-Butoxycarbonyl-S-acetamidomethylpenicillaminyl-1,2,3,4-tetrahydro-3(S)-isoquinolinecarbonyl-methionine Methylester To an ice-cooled solution of N-t-butoxycarbonyl-L-1,2,3,4-tetrahydro-3(S)-isoquinoline (2.77 g) and L-methionine methylester hydrochloride (2.0 g), 1-hydroxybenzotriazole (HOBT) (1.37 g) and O-Benzotriazol-1-yl-N,N,N',N'-tetramethyluronium hexafluorophosphate (HBTU) (3.87 g) in 30 ml dimethylformide was added 4.9 ml diisopropylethylamine (DIEA). After stirring at 0° C. for about 30 minutes, the reaction mixture was allowed to room temperature overnight. Volatile substances were evaporated in vacuo to dryness, and the residue was partitioned between EtOAc and water. EtOAc layer was washed with aqueous NaHCO₃, water, and dried (MgSO₄). Solvent was evaporated in vacuo to dryness. It was treated with 50% trifluoracetic acid in chloroform (40 ml) containing 4.8 ml triethylsilane for about 1 hour, and volatile substances were removed in vacuo to dryness. Trace of trifluoroacetic acid (TFA) was further evaporated with toluene. To the above L-1,2,3,4-tetrahydro-3(S)-isoquinolinecarbonyl methionine methylester TFA salt (2.2 g) in dichloromethane (20 ml) cooled to 0° C. was added 1.2 ml DIEA followed by a solution of HOBT (0.7 g), N-t-butoxycarbonyl-S-acetamidomethyl penicillin (1.6 g) in DMF (3 ml), and EDC (1.2 g). The mixture was stirred at 0° C. for about 30 minutes and then allowed to room temperature overnight. Volatile substances were removed in vacuo to dryness. The residue was partitioned between EtOAc and water. Ethylacetate layer was washed with aqueous NaHCO₃, water, and then dried (MgSO₄). Solvent was evaporated in vacuo to dryness to yield 3.3 g orange solid.

d) L-[S-acetamidomethylpenicillaminyl-1,2,3,4-tetrahydro-3[S]-isoquinolinecarbonyl Methionine Methylester and Its TFA Salt N-t-Butoxycarbonyl-S-acetamidomethyl-penicillaminyl-1,2,3,4-tetrahydro-3[S]-isoquinolinecarbonyl methionine methylester (3.3 g) was treated with 50% TFA in CH₂Cl₂ (20 ml) containing 1 ml triethylsilane for about 30 minutes Volatile substances were removed in vacuo to dryness. Trace of TFA was removed by co-evaporation with toluene several times. The TFA salt was dissolved in CHCl₃ (30 ml), treated with excess triethylamine, washed with water, dried (MgSO₄), and solvent was evaporated in vacuo to give free base.

e) N-[2(R)-(t-Butoxycarbonyl)amino-3-triphenylmethylmercaptopropyl]-L-[S-acetamidomethylpenicillaminyl]-1,2,3,4-tetrahydro-3(S)-isoquinolinecarbonyl Methionine Methyl Ester To a solution of 2(R)-t-butoxycarbonylamino-3-triphenyl methyl-mercapto-propanal (0.7 g) and L-[S-acetamido methylpenicillaminyl-1,2,3,4-tetrahydro-3(s)-isoquinolinecarbonyl methionine methylester (0.43 g) in CH₂Cl₂ (20 ml) containing 1% acetic acid was added triacetoxysodiumborohydride Na(OAc)₃BH (360 mg) in one portion. After stirring for about 2 hours, the mixture was washed with water, 5% aqueous NaHCO₃, water, and then dried (MgSO₄). The solvent was evaporated in vacuo to dryness, and the residue was chromatographed on silica gel (50 g) using CHCl₃/acetone (19:1 to 9:1) as eluants. Appropriate fractions were pooled and solvents were removed in vacuo to dryness resulting in a white foam (390 mg) of the above title compound. TLC (silica gel; CHCl₃/acetone=4:1; R$_f$=0.4).

f) N-[2(R)-(t-Butoxycarbonyl)amino-3-mercaptopropyl]-L-penicillaminyl]-1,2,3,4-tetrahydro-3(S)-isoquinoline Carbonyl Methionine Methylester Cyclic Disulfide To a solution of N-[2(R)-(t-butoxycarbonyl)amino-3-triphenylmethylmercaptopropyl]-L-[S-acetamidomethylpenicillaminyl]-1,2,3,4-tetrahydro-3(S)- isoquinoline carbonyl methionine methylester (500 mg) in 50 ml 90% aqueous MeOH was added dropwise a solution of iodine (250 mg) in methanol (MeOH) (10 ml). After stirring for about 1 hour, most of methanol was removed in vacuo to a small volume, diluted with water, and extracted with ethylacetate. The ethylacetate extract was washed with water, aqueous $Na_2S_2O_3$, water, and then dried ($MgSO_4$). The solvent was evaporated in vacuo to dryness resulting in 400 mg of the above title compound.

g) N-[2-(R)-Amino-3-mercaptopropyl]-L-penicillaminyl-1,2,3,4-tetrahydro-3(S)-isoquinoline Carbonyl Methionine Methylester Cyclic Disulfide Crude N-[2(R)-(t-butoxycarbonyl)amino-3-mercaptopropyl]-L-penicillaminyl-1,2,3,4-tetrahydro-3(S)-isoquinoline carbonyl methionine methylester cyclic disulfide (400 mg) was treated with 90% trifluoroacetic acid (TFA) in water $TFA/H_2O$ (9:1) (10 ml) for about 30 minutes Volatile substances were removed in vacuo to dryness, and a trace of TFA was evaporated with toluene several times and triturated with hexane, decanted, and then dried. Crude product was subjected to preparative high performance liquid chromatography (HPLC) using $C_{18}$ column and 0.1% TFA and $CH_3CN$ as mobile phase. Appropriate fractions were pooled, and solvents were removed giving the above title compound as a white solid (78 mg). M/e=541.1.

Example 2

Synthesis of N-[2-(R)-Amino-3-mercaptopropyl]-L-[s-acetamidomethyl-penicillaminyl]-1,2,3,4-tetrahydro-3(S)-isoquinoline Carbonyl Methionine (Compound 4)

To a solution of N-[2(R)-(t-butoxycarbonyl)-amino-3-triphenylmethylmercaptopropyl]-L-[s-acetamidomethyl penicillaminyl]-1,2,3,4-tetrahydro-3(S)-isoquinolinecarbonyl methionine methylester (Example I e))(500 mg) in 10 MeOH (50 ml) was added 2 ml 2 N-NaOH. After 30 minutes, most of MeOH was removed in vacuo to a small volume, diluted with water, acidified with 5% aqueous citric acid, and extracted with ethylacetate. The ethylacetate extract was then dried ($MgSO_4$). Solvent was evaporated in vacuo to dryness. The residue was treated with 50% TFA in $CH_2Cl_2$ containing triethylsilane ($Et_3SiH$) (0.5 ml) for about 40 minutes Volatile substances were removed in dryness, and a trace of TFA was evaporated with toluene and then dried. Crude product was purified by preparative HPLC giving the above titled compound (100 mg) as a white solid. M/e=600.2

Example 3

Synthesis of N-[2-(R)-Amino-3-mercaptopropyl]-L-penicillaminyl]-2,3-dimethylanilide Cyclic Disulfide (Compound 9)

a) [N-t-Butoxycarbonyl-S-acetamidomethyl]penicillaminyl-2,3-dimethylanilide

To an ice-cooled solution of N-[t-butoxycarbonyl)-S-acetamidomethyl penicillamine (Bachem California, Torrance, Calif.) (0.64 g), 2,3-dimethylaniline (0.25 g), hydroxybenzotriazole (0.41 g) in dimethylformide (DMF)/$CH_2Cl_2$ (1:1, 20 ml) was added 1-(3-dimethylaminopropyl)-3-ethylcarbodiimide (EDC) (0.57 g). The mixture was stirred at 0–5° C. for about 30 minutes and then the temperature was slowly allowed to room temperature overnight. After evaporation of the solvents, the residue was partitioned between ethyl acetate (EtOAc) and water. EtOAc extract was washed with aqueous $NaHCO_3$, water, and then dried ($MgSO_4$). The solvent was evaporated in vacuo to dryness. The residue was chromatographed on silica gel (40 g) using $CHCl_3$/acetone=19:1 as eluants, appropriate fractions were pooled, and solvents were removed in vacuo to dryness giving 350 mg of the above titled compound. TLC (silica gel: $CHCl_3$/acetone=4:1, $R_f$—0.77).

b) L-[S-acetamidomethylpenicillaminyl-2,3-dimethyl Anilide TFA Salt

[N-t-butoxycarbonyl-S-acetamidomethyl]-penicillaminyl-2,3-dimethylanilide was treated with 50% TFA in $CH_2Cl_2$ (20 ml) for about 30 minutes Volatile substances were removed in vacuo to dryness. Trace of TFA was removed by co-evaporation with toluene several times. The TFA salt was dissolved in $CHCl_3$ (30 ml), treated with excess triethylamine, washed with water, dried ($MgSO_4$), and solvent was evaporated in vacuo to give free base.

c) N-[2(R)-(t-Butoxycarbonyl)amino-3-triphenylmethylmercaptopropyl]-L-[S-acetamidomethylpenicillaminyl-2,3-dimethylamilide To a stirred solution of 2(R)-t-butoxycarbonylamino-3-triphenylmethylmercaptopropanal (0.5 g; Example 1b) and L-[S-acetamidomethylpenicillaminyl-2,3-dimethylanilide TFA salt (0.3 g) in MeOH containing 1% acetic acid (HOAc) (10 ml) was added portionwise $NaCNBH_3$ (100 mg). The mixture was stirred at room temperature overnight. Most of the solvent was evaporated in vacuo to a small volume, which was partitioned between EtOAc and water. EtOAc layer was further washed with aqueous $NaHCO_3$, water, and then dried ($MgSO_4$). After evaporation of solvent, the residue was chromatographed on silica gel (30 g) using $CHCl_3$-acetone (19:1 to 9:1) as eluants. Appropriate fractions were pooled, and solvents were evaporated in vacuo to dryness giving 360 mg of the above titled compound. TLC (silica gel: $CHCl_3$/acetone=9:1, $R_f$=0.13.

d) N-[2-(R)-Amino-3-mercaptopropyl]-L-penicillaminyl]-2,3-dimethylanilide Cyclic Disulfide To a stirred solution of N-[2(R)-(t-butoxycarbonyl) amino-3-triphenylmethylmercaptopropyl]-L-[S-acetamidomethyl penicillaminyl]-2,3-dimethylamilide (350 mg) in 50 ml 90% MeOH in water was added a solution of iodine (250 mg) in MeOH (5 ml). After 1 hour, most of the solvent was evaporated in vacuo to a small volume, diluted with water, extracted with EtOAc. EtoAc layer was washed with aqueous $Na_2S_{2O3}$, water, then dried ($MgSO_4$). Solvent was removed in vacuo to dryness (220 mg), treated with 90% aqueous TFA (ml) for about 30 minutes, and volatile substances were removed in vacuo to dryness. Crude product was purified by preparative HPLC giving 62 mg of the above titled compound as a white solid. M/e=340.2.

Example 4

Synthesis of 1-[2(R)-Amino-3-mercaptopropyl]-2 (S)-2-mercaptoethyl)-4-(1-naphthoyl)-piperazine-1,2-cyclodisulfide, (Compound 28), 1-[2(R)-Amino-3-mercaptopropyl]-2(S)-2-mercaptoethyl)-4-(1-naphthoyl)-piperazine, (Compound 30), and Bis-1,1'-2,2'-[2(R)-amino-3-mercaptopropyl]-2(S)-[2-mercaptoethyl)-4-(1-naphthoyl)-piperazine-tetrasulfide, (Compound 29)

a) Synthesis of 1-Benzyl-3(S)-benzyloxycarbonylmethyl piperazine-2,5-dione

To an ice-cooled solution of BOC-aspartic acid β-benzyl ester (10 g), hydroxybenzotriazole (HOBT, 4.2 g), and N-benzylglycine ethyl ester (6.4 g) in 80 ml $CH_2Cl_2$ was added a cold solution of dicyclohexylcarbodiimide (DCC, 7.1 g) in 20 ml $CH_2Cl_2$. The reaction was stirred for about 1 hour at 0–5° C., then overnight at room temperature. The precipitate was filtered off and the filtrate was evaporated in vacuo to dryness. The residue was partitioned between ethyl acetate and water. The organic layer was washed with 100 ml aqueous $NaHCO_3$, water, then dried ($MgSO_4$). Solvent was removed in vacuo to dryness to give 16 g. TLC (silica gel: $CHCl_3$/acetone=9:1, $R_f$=0.55).

This was treated with 50% trifluoroacetic acid in $CHCl_3$ (40 ml) for about 1 hour and the volatile substances were removed in vacuo to dryness. The residue was partitioned between ethyl acetate and saturated aqueous $NaHCO_3$. The organic layer was then dried ($MgSO_4$) and the solvent was evaporated in vacuo to give 10 g. TLC (silica gel, $CHCl_3$/acetone=9:1, $R_f$=0.14).

b) Synthesis of 4-Benzyl-1-tert-butoxycarbonyl-2(S)-(2-hydroxyethyl) piperazine

To an ice-cooled solution of the product from Step A (9.73 g) in 200 ml tetrahydrofuran (THF) was added portion wise a 50% mineral dispersion of lithium aluminum hydride (12.5 g) under a nitrogen atmosphere. The reaction mixture was refluxed overnight. After cooling in an ice bath, saturated aqueous $Na_2SO_4$ was added dropwise to decompose excess LAH and the white slurry in THF was filtered through a diatomaceous earth pad. The filtrate was concentrated in vacuo to dryness and the residue was dissolved in dichloromethane (55 mg), treated with di-tert-butyl dicarbonate (5.9 g), and stirred for about 1 hour. Aqueous saturated $NaHCO_3$ (25 ml) was added and stirred for about 2 hours. The organic layer was washed with saturated sodium chloride and dried ($MgSO_4$). After evaporation of solvent, the residue was chromatographed on silica gel (160 g) using $CHCl_3$/MeOH (19:1) as eluent. Appropriate fractions were pooled, and solvents were removed in vacuo to dryness, to give 8.7 g of a glass. TLC (silica gel: $CHCl_3$/MeOH=9:1, $R_f$=0.56).

c) Synthesis of 1-tert-Butoxycarbonyl-2-(S)-(2-hydroxyethyl) piperazine

The product from Step B (8.7 g) was dissolved in ethanol (35 ml) treated with $Pd(OH)_2$-charcoal (0.8 g) and acetic acid (3 ml). Hydrogenation was carried out under 30 p.s.i. overnight. The reaction mixture was filtered through a diatomaceous earth pad and the solvent was removed in vacuo to dryness.

d) Synthesis of 1-tert-Butoxycarbonyl-2(S)-(2-hydroxyethyl)-4-(1-naphthoyl) piperazine To a solution of the product from Step C (8.4 g) in acetonitrile (40 ml) was added 110 ml 1N aqueous NaOH followed by a solution of 1-naphthoyl chloride (5.14 g) in acetonitrile (20 ml). After about 3 hours stirring, most of the acetonitrile was removed in vacuo and the remaining mixture was extracted with chloroform. It was dried ($MgSO_4$) and the solvent was removed in vacuo to dryness, to give 8.12 g. of product. TLC (silica gel: $CHCl_3$/MeOH=9:1, $R_f$=0.64).

e) Synthesis of 1-tert-Butoxycarbonyl-2(S)-(2-triphenylmethylthioethyl)-4-(1-naphthoyl)piperazine To an ice-cooled solution of triphenylphosphine (0.53 g) in 5 ml dry THF was added dropwise a solution of diethylazodicarboxylate (DEAD, 0.25 g) in 2 ml THF. After stirring at 0–5° C. for about 30 minutes, a solution of the product from Step D (0.4 g) and triphenylmercaptan (0.55 g) in 10 ml THF was added dropwise. The mixture was stirred at 0–5° C. for about 1 hour and room temperature for about 1 hour. The solvent was evaporated in vacuo to dryness and the residue was chromatographed on silica gel (40 g) using $CHCl_3$ as eluent. Appropriate fractions were pooled and the solvent was removed in vacuo to dryness, to give a pale yellow foam 420 mg. Mass Spec (Electrospray) 665.2 (643+23(sodium)). TLC (silica gel: $CHCl_3$/acetone=9:1 $R_f$=0.53)

f) Synthesis of 2(S)-(2-Triphenylmethylthioethyl)-4-(1-naphthoyl) piperazine

To a stirred solution of the product from Step E (2.2 g) in 30 ml $CH_2Cl_2$ was added 10 ml trifluoroacetic acid (TFA). The mixture was stirred for about 30 minutes. Volatile substances were removed in vacuo to dryness. The residue was dissolved in $CHCl_3$ (50 ml) and treated with excess triethylamine (4 ml). The mixture was washed with water, then dried ($MgSO_4$) and volatile substances were removed in vacuo to dryness, to give a pale yellow glass, 2.1 g; TLC (silica gel; $CHCl_3$/MeOH=9:1, $R_f$=0.63)

g) Synthesis of 1-[2(R)-N-tert-Butoxycarbonylamino-3-triphenyl methylthiopropyl]-2(S)-(2-triphenylmethylthioethyl)-4-(1-naphthoyl)-piperazine To a solution of the product from Step F (0.9 g) and 2(R)-N-tert-butoxycarbonylamino-3-triphenylmethylthiopropanal (1.2 g) prepared according to the procedure of O. P. Goel, et al., (Org. Syn. 1988, 67, 69–75), in $CH_2Cl_2$ (20 ml) containing 1% acetic acid, was added 4 g of molecular sieves 4 Å followed by portion wise addition of $Na(OAc)_3BH$ (1 g) over a 30 minutes period. After stirring for about 2 hours, the mixture was filtered and the filtrate was washed with water, 5% aqueous $NaHCO_3$, water, and then dried ($MgSO_4$). The solvent was evaporated in vacuo to dryness, and the residue was chromatographed on silica gel (60 g) using $CHCl_3$ as an eluent. Appropriate fractions were pooled and solvent was removed in vacuo to dryness, to give 0.6 g white foam. TLC (silica gel, $CHCl_3$/acetone=9:1; $R_f$=0.55); Mass Spec (Electro Spray) 974.3.

h) Synthesis of 1-[2(R)-amino-3-mercaptopropyl]-2(S)-2-mercaptoethyl)-4-(1-naphthoyl)-piperazine-1,2-cyclodisulfide, (Compound 28), and Bis-1,1'-2,2'-[2(R)-Amino-3-mercaptopropyl]-2(S)-[2-mercaptoethyl)-4-(1-naphthoyl)-piperazine-tetrasulfide, (Compound 29)

To a stirred solution of the product from step g (0.7 g) in $CHCl_3/CH_3OH$ (1:3, 60 ml) was added a solution of iodine in methanol (0.2 g in 5 ml). After stirring for about 40 minutes most of the solvents were removed in vacuo to dryness and the residue was partitioned between ethyl acetate (30 ml) and 5% aqueous $Na_2S_2O_3$. The organic layer was washed with water, then dried ($MgSO_4$). After evaporation of solvent the residue was treated with 50% trifluoroacetic acid in dichloromethane (10 ml) for about 30 minutes. Volatile substances were removed in vacuo to dryness and the residue was triturated with ether and filtered.

The crude product was subjected to preparative high performance liquid chromatography (HPLC) using a $C_{18}$ column and 0.1% aqueous TFA and $CH_3CN$ as the mobile phase. Earlier fractions (retention=5 minutes, $CH_3CN$/0.1% aqueous TFA=50:50, elution rate=1 ml/min) gave the white solid 1,2 cyclodisulfide; Mass. Spec. (Electrospray)=388.1. Later fractions (retention time=7.2 minutes using the same isocratic conditions) gave the dimer; Mass Spec. (Electrospray)=775.1 The ratio of cyclic disulfide and dimeric tetrasulfide was about 4 to 1.

Example 5

Alternative Cyclization of compound 30 Using Immobilized Oxidizing Resin (EKATHIOX™ Resin) or Air a) Synthesis of 1-[2(R)-Amino-3-mercaptopropyl]-2(S)-2-mercaptoethyl)-4-(1-naphthoyl)-piperazine (Compound 30)

The product from Step G (450 mg) was treated for about 30 minutes with 50% TFA in $CH_2Cl_2$ (10 ml) containing 1 ml triethylsilane. Volatile substances were then removed in vacuo to dryness. The residue was triturated with ether, filtered, then dried, resulting in 280 mg of 1-[2(R)-amino-3-mercaptopropyl]-2(S)-(2-mercaptoethyl)-4-(1-naphthoyl)-piperazine, (Compound 30). Mass spec (electrospray) 390.3 b) Cyclization of 1-[2(R)-Amino-3-mercaptopropyl]-2(S)-2-mercaptoethyl)-4-(1-naphthoyl)-piperazine (Compound 30) to form 1-[2(R)-Amino-3-mercaptopropyl]-2(S)-2-mercaptoethyl)-4-(1-naphthoyl)-piperazine-1,2-cyclodisulfide (Compound 28)

100 mg of the product from Step a) was dissolved in 10 ml aqueous $CH_3CN$ ($H_2O/CH_3CN$=7.3), and treated with 3 g of EKATHIOX™ resin (0.34 mmoles/gm). The mixture was stirred at room temperature for about 6 hours. The mixture was then filtered, the resin washed with aqueous methanol (1:3), and most of the organic solvent was removed in vacuo to a small volume. The concentrate was subjected to preparative HPLC using 0.1% aqueous TFA and $CH_3CN$ as mobile phase. Appropriate fractions were pooled and most of the solvents removed in vacuo to small volume. The concentrate was then lyophilized.

Alternatively, the solution of 1-[2(R)-amino-3-mercaptopropyl]-2(S)-(2-mercaptoethyl)-4-(1-naphthoyl)-piperazine (Compound 30) in aqueous $CH_3CN$ was stirred with air in pH 6–8 range. In both instances the reaction mixture showed a distribution of the cyclic disulfide and the tetrasulfide dimer in the ratio of about 4 to 1.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:
1. A compound of formula III or formula IV;

Formula III

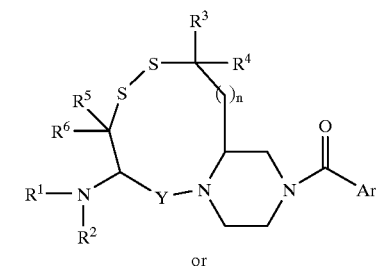

or

Formula IV

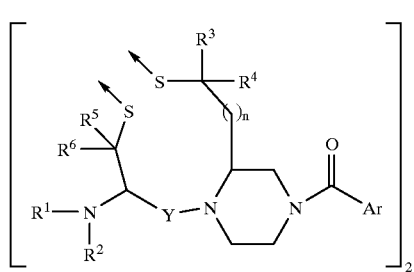

wherein

Y is $CH_2$ or $C(O)$;

$R^1$, $R^2$, $R^3$, and $R^4$, each is, independently, H, lower alkyl, or an optionally substituted moiety selected from the group consisting of arylalkyl, alkenyl, $(C_1$–$C_{18})$-aliphatic acyl, and arylacyl;

$R^5$ and $R^6$ each is, independently, H or $CH_3$;

$R_9$ and $R_{10}$ each is independently selected from the group consisting of H, lower alkyl, and $(C_3$–$C_6)$ cycloalkyl;

Ar is an optionally substituted moiety selected from the group consisting of aryl and heterocycle;

n is 0 or an integer from 1 to 4;

wherein each optionally substituted moiety is optionally substituted by one or more substituent independently selected from the group consisting of aryl, heterocycle, halogen, $OR^9$, $NR^9R^{10}$, CN, $NO_2$, $CF_3$, or lower alkyl, said lower alkyl optionally substituted with $(C_1$–$C_4)$-alkoxy, $NR^9R^{10}$, $(C_3$–$C_6)$-cycloalkyl, or OH;

or a pharmaceutically acceptable salt thereof.

2. A compound of claim 1, wherein said compound is of formula IV, or a pharmaceutically acceptable salt thereof.

3. A compound of claim 2, wherein Y is $C(O)$; or a pharmaceutically acceptable salt thereof.

4. A compound of claim 1, wherein said compound is of the formula

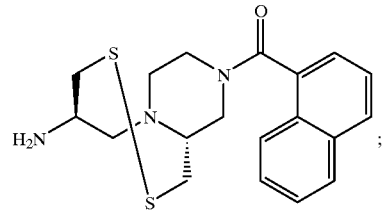

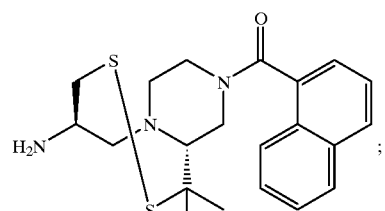

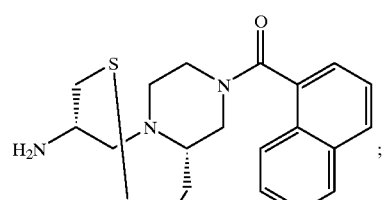

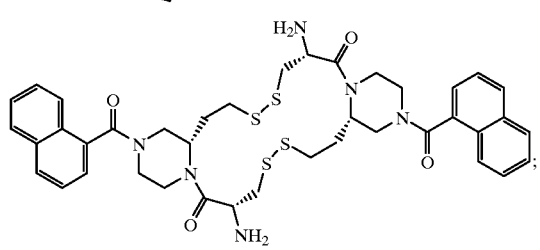

-continued

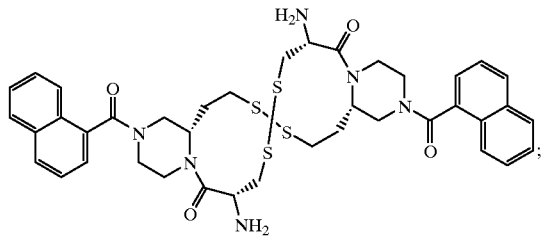

or

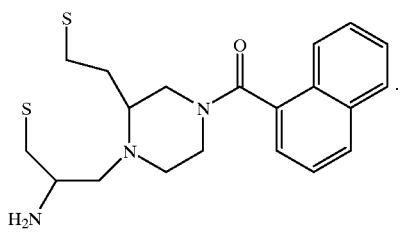

5. A method of treating tumors or restenosis in a subject in need of said treatment, which comprises administering to said subject a therapeutically effective amount of a compound or salt of claim 1.

6. A method of treating tumors or restenosis in a subject in need of said treatment, which comprises administering to said subject a therapeutically effective amount of a compound or salt thereof according to claim 4.

7. A pharmaceutical composition comprising a therapeutically effective amount of a compound of claim 1 and a pharmaceutically acceptable carrier.

* * * * *